(12) United States Patent
Miller et al.

(10) Patent No.: US 8,147,523 B2
(45) Date of Patent: Apr. 3, 2012

(54) OFFSET VERTEBRAL ROD CONNECTOR

(75) Inventors: Keith E. Miller, Germantown, TN (US); Lauren I. Lyons, San Francisco, CA (US)

(73) Assignee: Warsaw Orthopedic, Inc., Warsaw, IN (US)

(*) Notice: Subject to any disclaimer, the term of this patent is extended or adjusted under 35 U.S.C. 154(b) by 710 days.

(21) Appl. No.: 12/206,889

(22) Filed: Sep. 9, 2008

(65) Prior Publication Data

US 2010/0063546 A1    Mar. 11, 2010

(51) Int. Cl.
*A61B 17/70* (2006.01)

(52) U.S. Cl. .................................... 606/278

(58) Field of Classification Search ........... 606/246–279
See application file for complete search history.

(56) References Cited

U.S. PATENT DOCUMENTS

| | | | |
|---|---|---|---|
| 4,569,338 A | 2/1986 | Edwards | |
| 4,827,918 A | 5/1989 | Olerud | |
| 5,047,029 A | 9/1991 | Aebi | |
| 5,053,034 A | 10/1991 | Olerud | |
| 5,176,680 A | 1/1993 | Vignaud | |
| 5,254,118 A | 10/1993 | Mirkovic | |
| 5,352,226 A | 10/1994 | Lin | |
| 5,466,237 A * | 11/1995 | Byrd et al. | 606/272 |
| 5,487,744 A * | 1/1996 | Howland | 606/264 |
| 5,527,314 A | 6/1996 | Brumfield | |
| 5,534,002 A | 7/1996 | Brumfield | |
| 5,562,662 A | 10/1996 | Brumfield | |
| 5,575,791 A | 11/1996 | Lin | |
| 5,643,263 A | 7/1997 | Simonson | |
| 5,733,285 A | 3/1998 | Errico | |
| 5,885,285 A | 3/1999 | Simonson | |
| 5,938,663 A | 8/1999 | Petreto | |
| 5,947,967 A | 9/1999 | Barker | |
| 6,001,098 A | 12/1999 | Metz-Stavenhagen | |
| 6,183,473 B1 | 2/2001 | Ashman | |
| 6,183,476 B1 | 2/2001 | Gerhardt | |
| 6,187,005 B1 | 2/2001 | Brace | |
| 6,210,413 B1 | 4/2001 | Justis | |
| 6,248,104 B1 | 6/2001 | Chopin | |
| 6,248,107 B1 | 6/2001 | Foley | |
| 6,402,749 B1 | 6/2002 | Ashman | |
| 6,471,703 B1 | 10/2002 | Ashman | |

(Continued)

FOREIGN PATENT DOCUMENTS

WO    2005122965    12/2005

(Continued)

OTHER PUBLICATIONS

International Searching Authority, International Search Report and Written Opinion, Feb. 23, 2010.

*Primary Examiner* — Eduardo C Robert
*Assistant Examiner* — Stuart S Bray (57) ABSTRACT

The present application is directed to connectors for attaching a vertebral rod to an anchor. The connectors may include a body with a first channel to receive the vertebral rod and a second channel to receive the anchor. A cradle may be positioned in the body to contact the vertebral rod. The cradle may be pivotally positioned in the body to accommodate a vertebral rod that is at various angular positions within a predetermined plane. A set screw may engage with the body to secure the vertebral rod to the body and the body to the anchor.

8 Claims, 14 Drawing Sheets

U.S. PATENT DOCUMENTS

| | | |
|---|---|---|
| 6,520,962 B1 | 2/2003 | Taylor |
| 6,562,038 B1 | 5/2003 | Morrison |
| 6,579,292 B2 | 6/2003 | Taylor |
| 6,626,906 B1 | 9/2003 | Young |
| 6,673,074 B2 | 1/2004 | Shluzas |
| 6,685,705 B1 | 2/2004 | Taylor |
| 6,709,434 B1 | 3/2004 | Gournay |
| 6,716,214 B1 | 4/2004 | Jackson |
| 6,872,209 B2 | 3/2005 | Morrison |
| 7,066,939 B2 | 6/2006 | Taylor |
| 7,270,665 B2 | 9/2007 | Morrison |
| 2002/0193794 A1 | 12/2002 | Taylor |
| 2003/0176862 A1 | 9/2003 | Taylor |
| 2004/0010253 A1 | 1/2004 | Morrison |
| 2004/0092930 A1 | 5/2004 | Petit |
| 2005/0038433 A1 | 2/2005 | Young |
| 2006/0058787 A1* | 3/2006 | David ................ 606/61 |
| 2007/0161995 A1 | 7/2007 | Trautwein |
| 2007/0233063 A1 | 10/2007 | Rezach |
| 2007/0233066 A1 | 10/2007 | Rezach |
| 2008/0195122 A1* | 8/2008 | Castellvi et al. .......... 606/151 |

FOREIGN PATENT DOCUMENTS

| | | |
|---|---|---|
| WO | 2006119237 | 11/2006 |

\* cited by examiner

OFFSET VERTEBRAL ROD CONNECTOR

BACKGROUND

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve.

A vertebral rod may be implanted to support and position a vertebral member in one or more of these regions. The vertebral rod extends along a section of the spine and may have a curved configuration to conform to the curvature and contour of the spine. The vertebral rod is connected to the spine with one or more anchors.

The anchors are inserted into the vertebral members to attach the vertebral rod. A connector attaches the vertebral rod to the anchor. The connector should be able to attach the vertebral rod and anchor when they are at a variety of different angular positions which is caused by factors such as the variably contoured surfaces of the vertebral members and the curvature and orientation of the vertebral rods.

The connector should provide a secure attachment of the vertebral rod to the anchor. The connector should also position the vertebral rod relative to the anchor to prevent the anchor from loosening from its purchase within the vertebral member when forces are applied to the vertebral rod.

SUMMARY

The present application is directed to connectors for attaching a vertebral rod to an anchor. The connectors may include a body with a first channel to receive the vertebral rod and a second channel to receive the anchor. A cradle may be positioned in the body to contact against the vertebral rod. The cradle may be pivotally positioned in the body to accommodate a vertebral rod that is in various angular positions within a predetermined plane. A set screw may engage with the body to secure the vertebral rod to the body and the body to the anchor.

The aspects of the various embodiments may be used alone or in any combination, as is desired.

DETAILED DESCRIPTION

Figure 1:
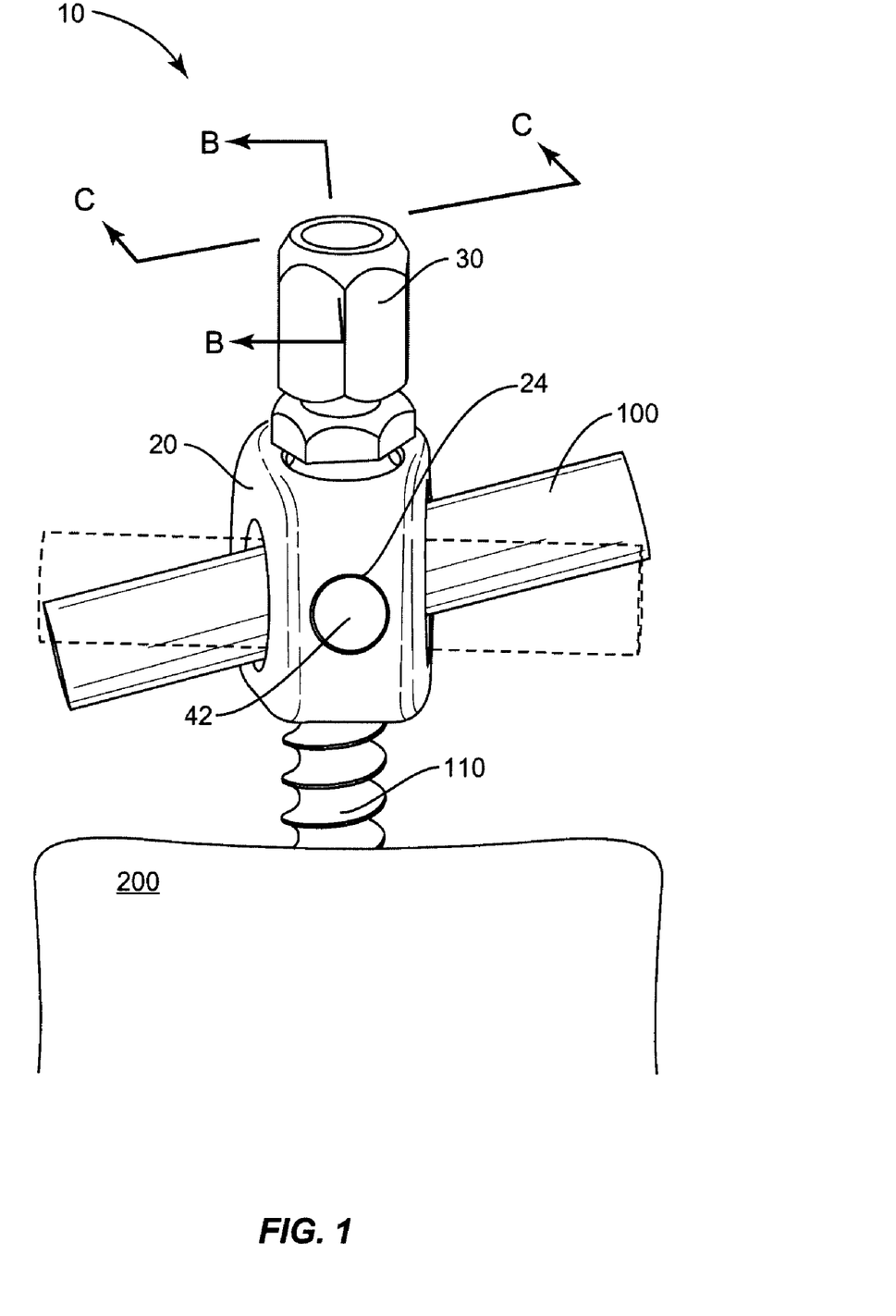
FIG. 1 is a perspective view of a connector that attaches a vertebral rod to an anchor according to one embodiment.

The present application is directed to offset vertebral connectors that attach a vertebral rod to a vertebral member. FIG. 1 includes one embodiment of a connector 10 that positions a vertebral rod 100 at an offset from an anchor 110. The connector 10 may provide for a single step to securely attach both the vertebral rod 100 and the anchor 110. The connector 10 is also configured to accommodate the vertebral rod 100 at a variety of angles within a designated plane. In one embodiment, the designated plane is the sagittal plane. The connector 10 positions the vertebral rod 100 in proximity to the anchor 110 to prevent the anchor 100 from turning within the vertebral member 200 due to forces applied from axial compression and bending of the vertebral rod 100.

Figure 2A:
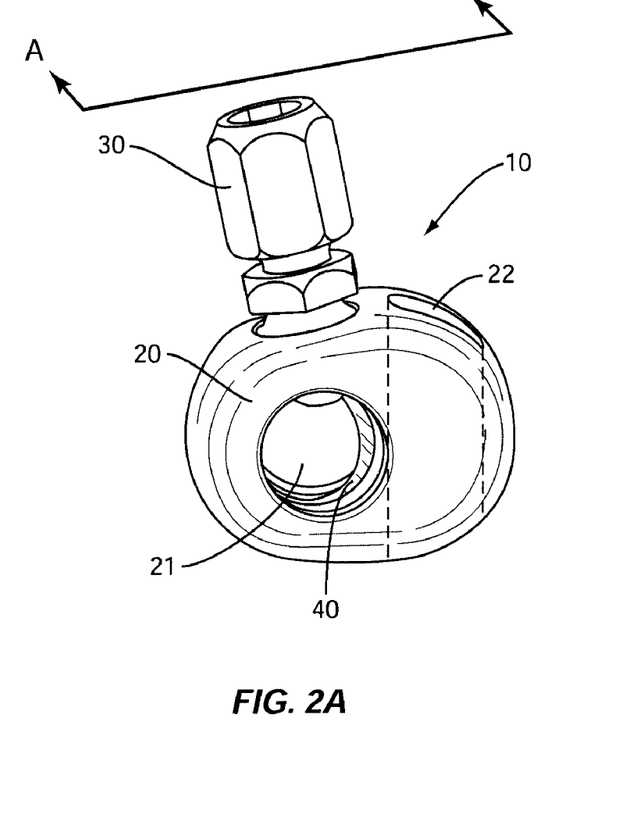
FIG. 2A is a perspective view of a connector according to one embodiment.
Figure 2B:
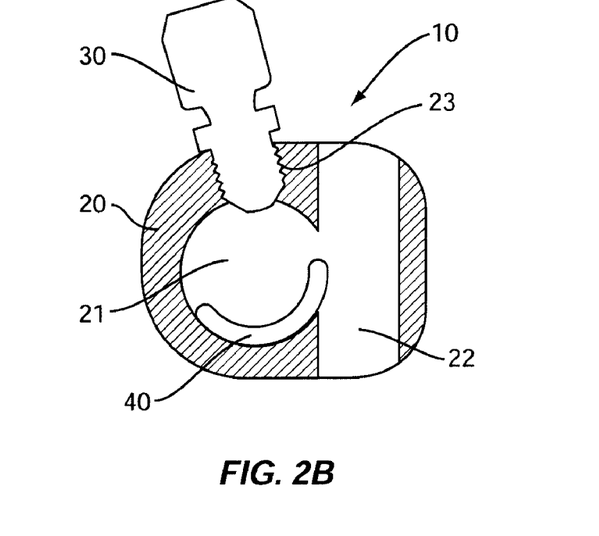
FIG. 2B is a sectional view of the connector of FIG. 2A cut along line A-A.

FIGS. 2A and 2B illustrate an embodiment of a connector 10 that includes a body 20, set screw 30, and cradle 40. The body 20 includes a first channel 21 that extends in a first plane and a second channel 22 that extends in a second plane. The first channel 21 is sized to receive the vertebral rod 100, and the second channel 22 to receive the anchor 110. A centerline of the first channel 21 is offset from a centerline of the second channel 22 to position the vertebral rod 100 at an offset from the anchor 110. The cradle 40 is positioned to contact against the vertebral rod 100 and allow the vertebral rod 100 to be positioned at various angles within the designated plane. The set screw 30 attaches to the body 20 to lock the vertebral rod 100 to the body 20, and lock the body 20 to the anchor 110.

The body 20 is sized to include the first and second channels 21, 22. The first channel 21 may include an enlarged shape that is larger than the vertebral rod 100 to allow the rod to pivot within the body 20 and be positioned at a variety of angular positions relative to the first and second planes. The first channel 21 may extend through a first pair of sides of the body 20, and the second channel 22 through a second pair of sides. In one embodiment as illustrated in FIG. 1, the first pair of sides may include lateral sides, and the second pair may include superior and inferior sides. The channels 21, 22 may be positioned with centerlines of the channels 21, 22 being offset. The first and second channels 21, 22 may be in communication, or may be separated within the body 20.

Figure 5:
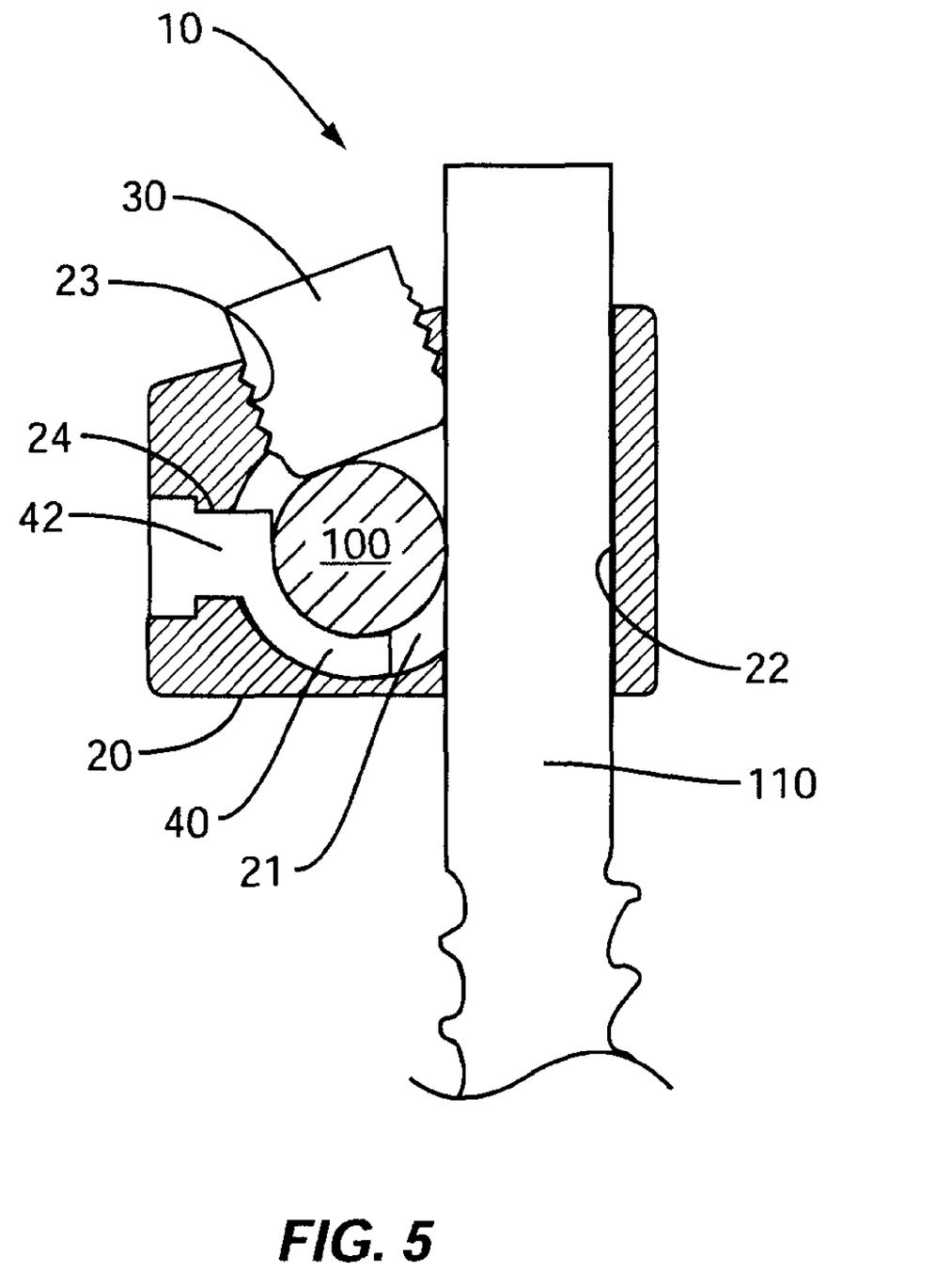
FIG. 5 is a sectional view of a connector that attaches a vertebral rod to an anchor according to one embodiment.

Body 20 also includes an opening 23 to receive the set screw 30. The opening 23 extends through the body to position the set screw 30 into the first channel 21 to contact against the vertebral rod 100. In one embodiment, the opening 23 is configured to position the set screw 30 away from the second channel 22. In one embodiment, the opening 23 is parallel with the centerline of the second channel 22. The opening 23 may also be positioned for the set screw 30 to extend into the second channel 22 as illustrated in FIG. 5 to contact against the anchor 110. The opening 23 may include threads that engage with threads 33 on the set screw 30. Opening 23 may also be tapered with a decreasing width positioned away from the second channel 22. The tapered configuration may cause the set screw 30 to lock into position in the tapered opening 23 when a force is applied to the connector 10.

Figure 16:
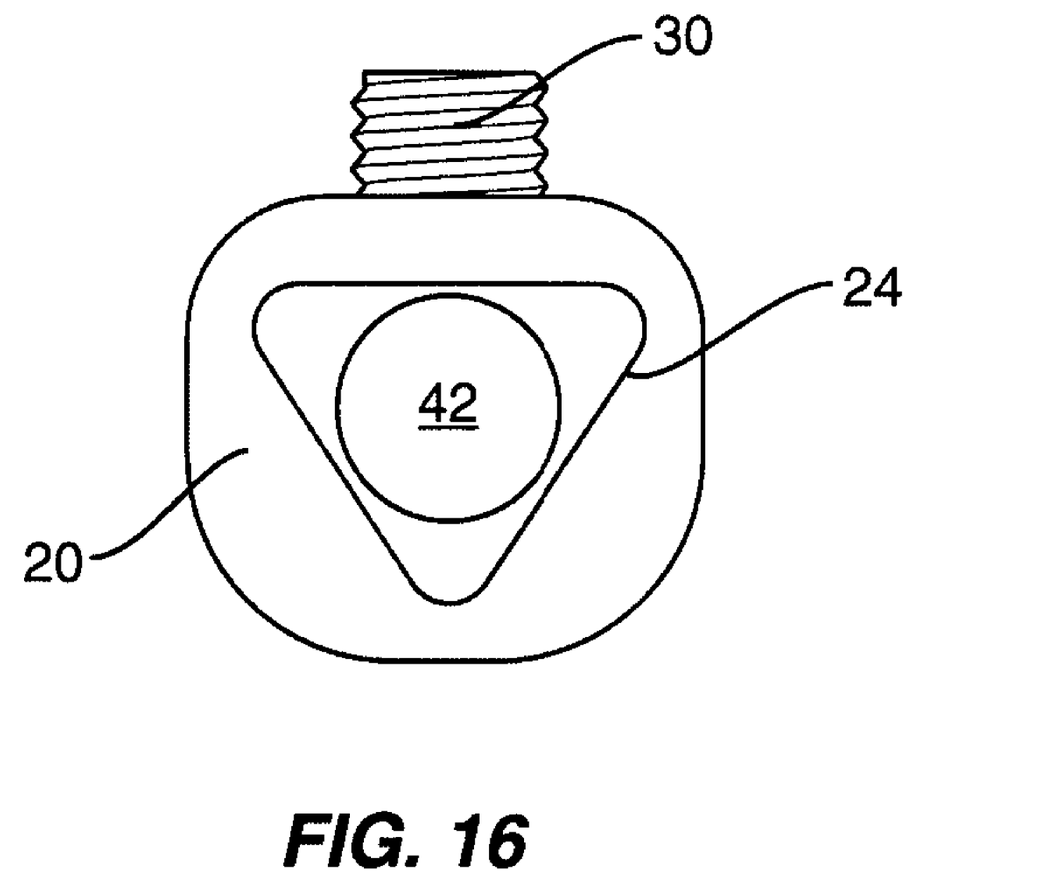
FIG. 16 is a schematic side view of a body with a tapered opening to receive a post of the cradle according to one embodiment.
Figure 17:
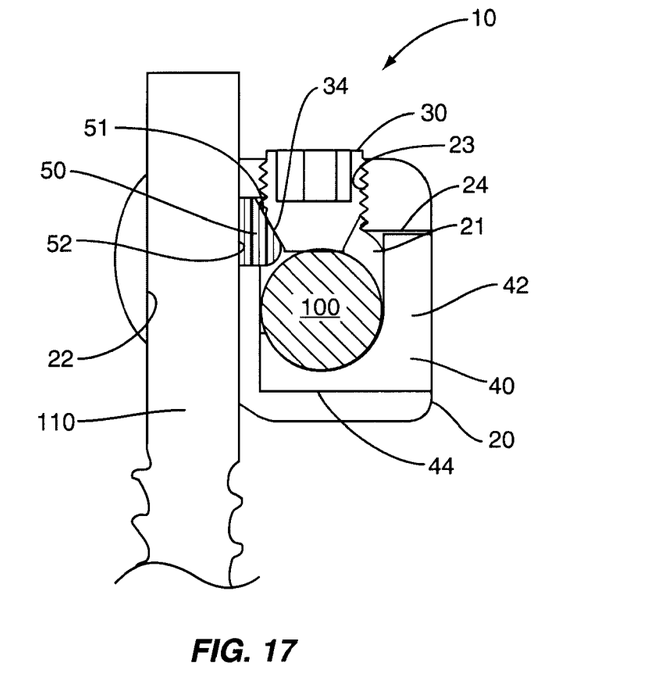
FIG. 17 is a sectional view of a connector that attaches a vertebral rod to an anchor according to one embodiment.
Figure 18:
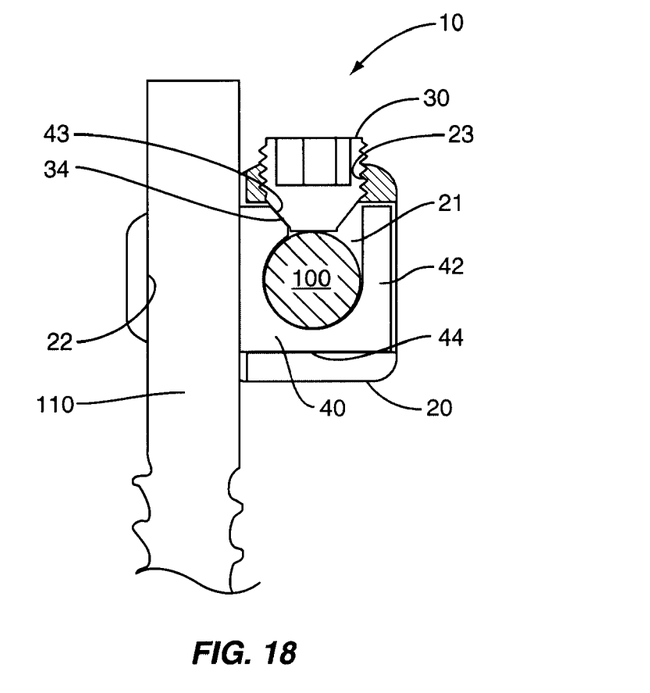
FIG. 18 is a sectional view of a connector that attaches a vertebral rod to an anchor according to one embodiment.

Body 20 may also include an opening 24 to receive a post 42 of the cradle 40 as will be explained below. The opening 24 may be substantially the same size as the post 42 as illustrated in FIG. 1 to prevent translational movement of the post 42 but allow rotational movement. The opening 24 may also be larger than the post 42 to allow for translational and/or rotational movement. FIG. 16 includes the opening 24 with a tapered configuration with a decreasing width. When the set screw 30 is tightened, the post 42 is pushed into the tapered opening 24 thereby locking the angulation of the cradle 40. The opening 24 may also be substantially the same size as a side of the body 20 as illustrated in FIGS. 17 and 18.

The set screw 30 attaches to the body 20 to apply a force to secure the body 20 to the vertebral rod 100, and the body 20 to the anchor 110. The set screw 30 is movable between disengaged and engaged positions. The disengaged position results in no force being applied to the rod 100 or anchor 110, while the engaged position results in a force being applied to the rod 100 and anchor 110. In the engaged position, the set screw 30 may extend outward beyond the body 20, or may be recessed within the body 20. The disengaged position may include the set screw 30 being removed from the body 20, or remaining attached to the body 20.

Set screw 30 may include a head 31 and a shaft 32. The head 31 may include a polygonal sectional shape and/or a receiver to engage with a tightening tool such as a screwdriver or wrench. The shaft 32 may include threads 33 that engage with corresponding threads on the body opening 23. A contact surface 34 is positioned at an end of the shaft 32 to contact against one or more of the vertebral rod 100, cradle 40, piston 50, and anchor 110. The contact surface 34 may be positioned at one or more angles relative to a longitudinal axis of the shaft 32, including perpendicular and oblique. The end of the shaft 32 may include a conical shape that includes angled contact surfaces 34. The set screw 30 may also include a variety of geometries to engage with one or more of the vertebral rod 100, anchor 110, piston 50, and cradle 40. These include but are not limited to a nub, boss protrusion, and a flat bottom.

Figure 3:
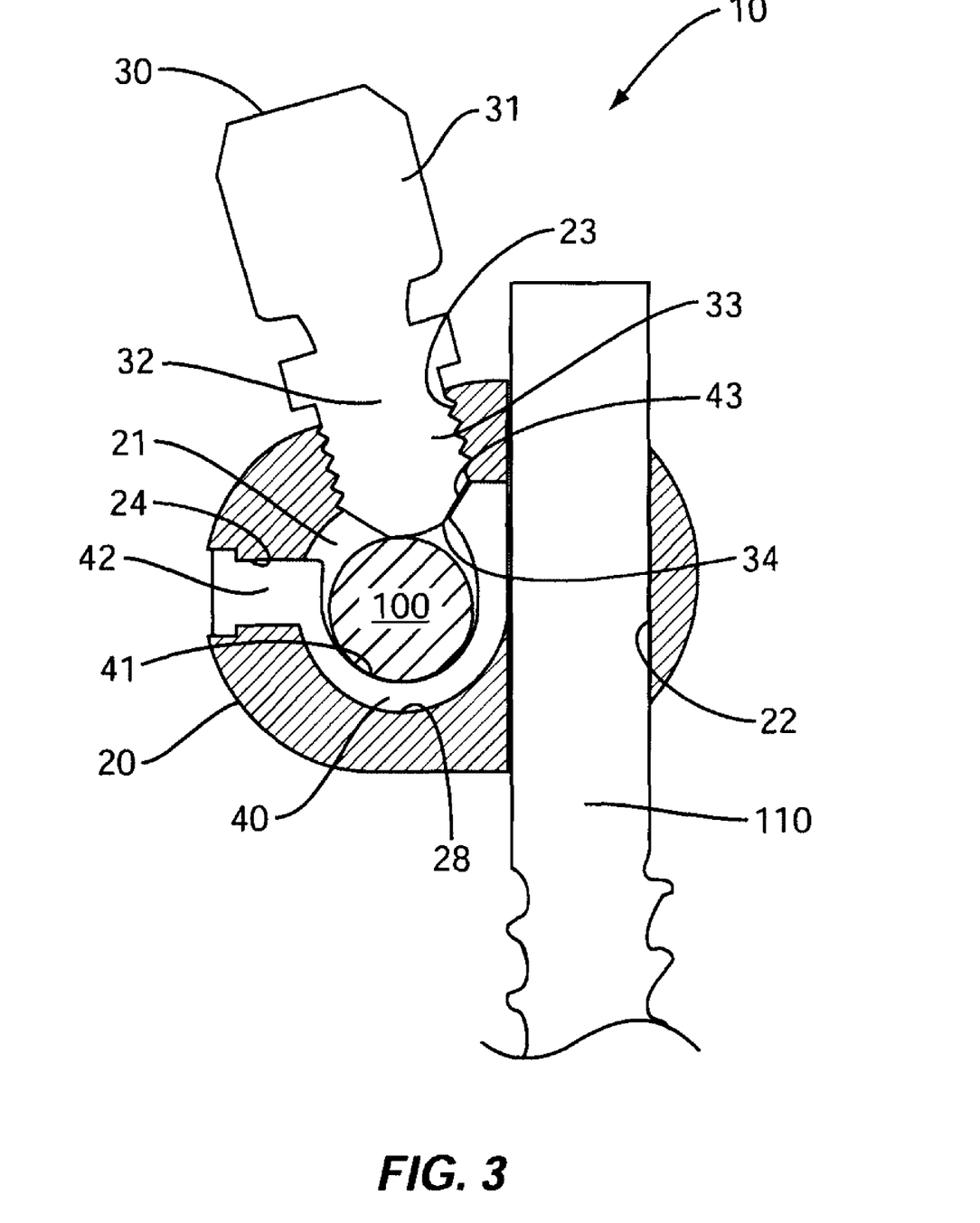
FIG. 3 is a sectional view of a connector the connector of FIG. 1 cut along line B-B.
Figure 7:
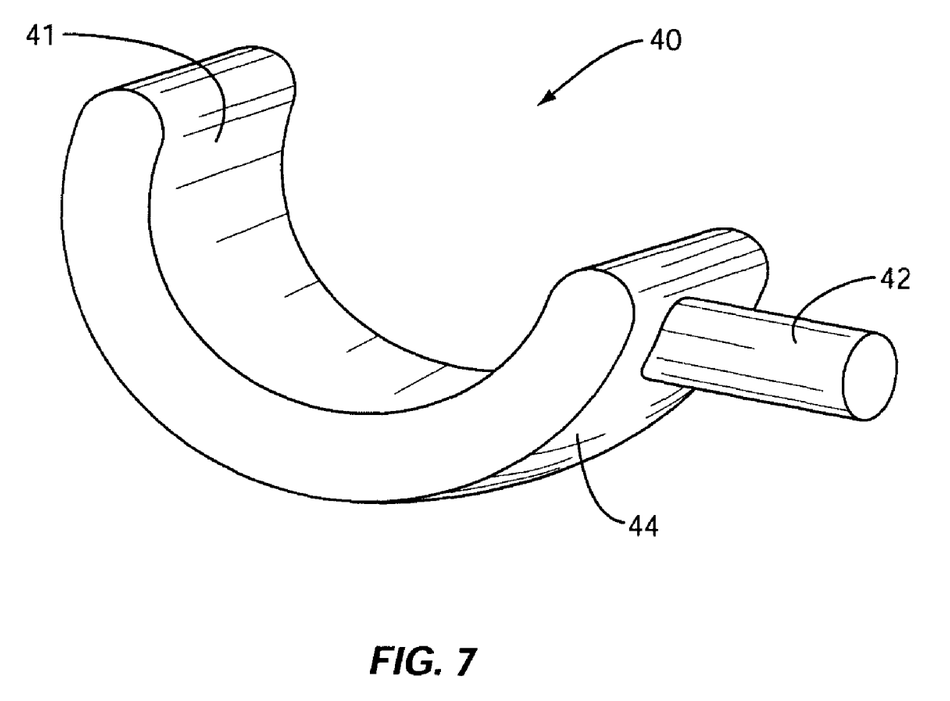
FIG. 7 is a perspective view of a cradle according to one embodiment.

The cradle 40 is movably positioned in the body 20 to position the vertebral rod 100 at a variety of angles within the designated plane. The cradle 40 may be partially or completely positioned in the body 20. FIG. 7 includes one embodiment of the cradle 40 that includes a first surface 41 that forms a receptacle that contacts against the vertebral rod 100. The first surface 41 may include a curved shape that approximates the sectional shape of the vertebral rod 100. In one embodiment, the first surface 41 forms an arc that is greater than 180 degrees to extend around a majority of the vertebral rod 100. The first surface 41 may also include other shapes depending upon the sectional shape of the vertebral rod 100. The shape of the first surface 41 may either approximate or purposefully differentiate from the sectional shape of the vertebral rod 100. The first surface 41 may include a length to extend around a majority of the vertebral rod 100 as illustrated in FIGS. 3 and 18, or around a limited peripheral section of the vertebral rod 100 as illustrated in FIG. 5. A second surface 44 may contact against the body 20. The second surface 44 may include a rounded shape to facilitate positioning of the cradle 40 at various angular positions within the body 20.

Figure 9:
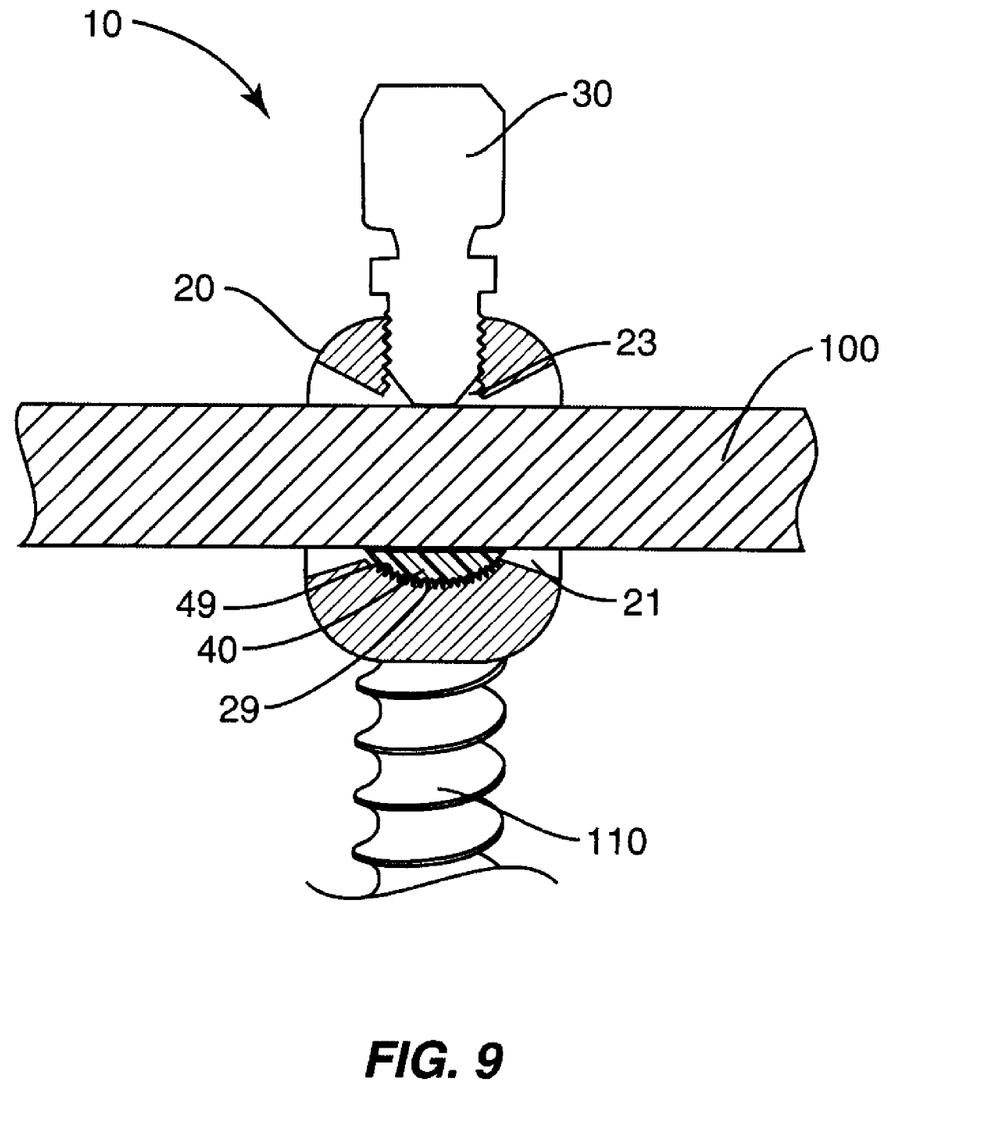
FIG. 9 is a sectional view of a connector the connector of FIG. 1 cut along line C-C.

When the set screw 30 is tightened, the cradle 40 can be secured relative to the body 20 in several different manners. FIG. 9 includes the cradle 40 with splines 49 along the second surface 44 an outer surface that engage corresponding splines 29 in the body 20. The splines 49, 29 may be perpendicular to the first channel 21. In another embodiment, the body 20 includes one or more undulations 28 that extend into the first channel 21 sized to receive the second surface 44 of the cradle 40. The cradle 40 is positioned at the appropriate angle relative to the body 20 and held in the appropriate ridge when the set screw 30 is tightened. In one embodiment, the undulation 28 is centered on the centerline of the first opening 23.

These various embodiments may be used individually, or in various combinations. In one embodiment, the cradle 40 can be positioned within an angulation range of about ±50 degrees relative to the body 20.

Figure 4:
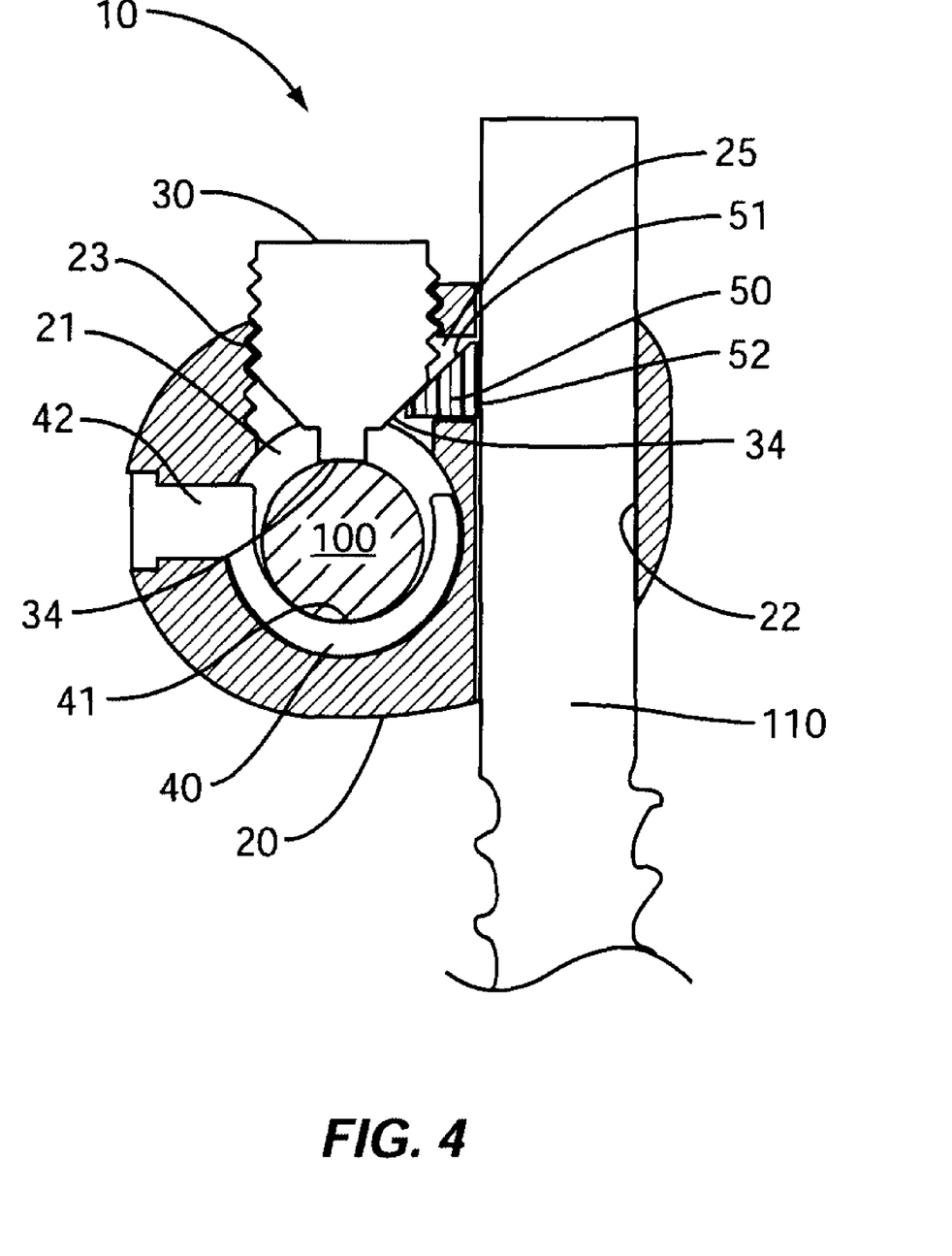
FIG. 4 is a sectional view of a connector that attaches a vertebral rod to an anchor according to one embodiment.
Figure 6:
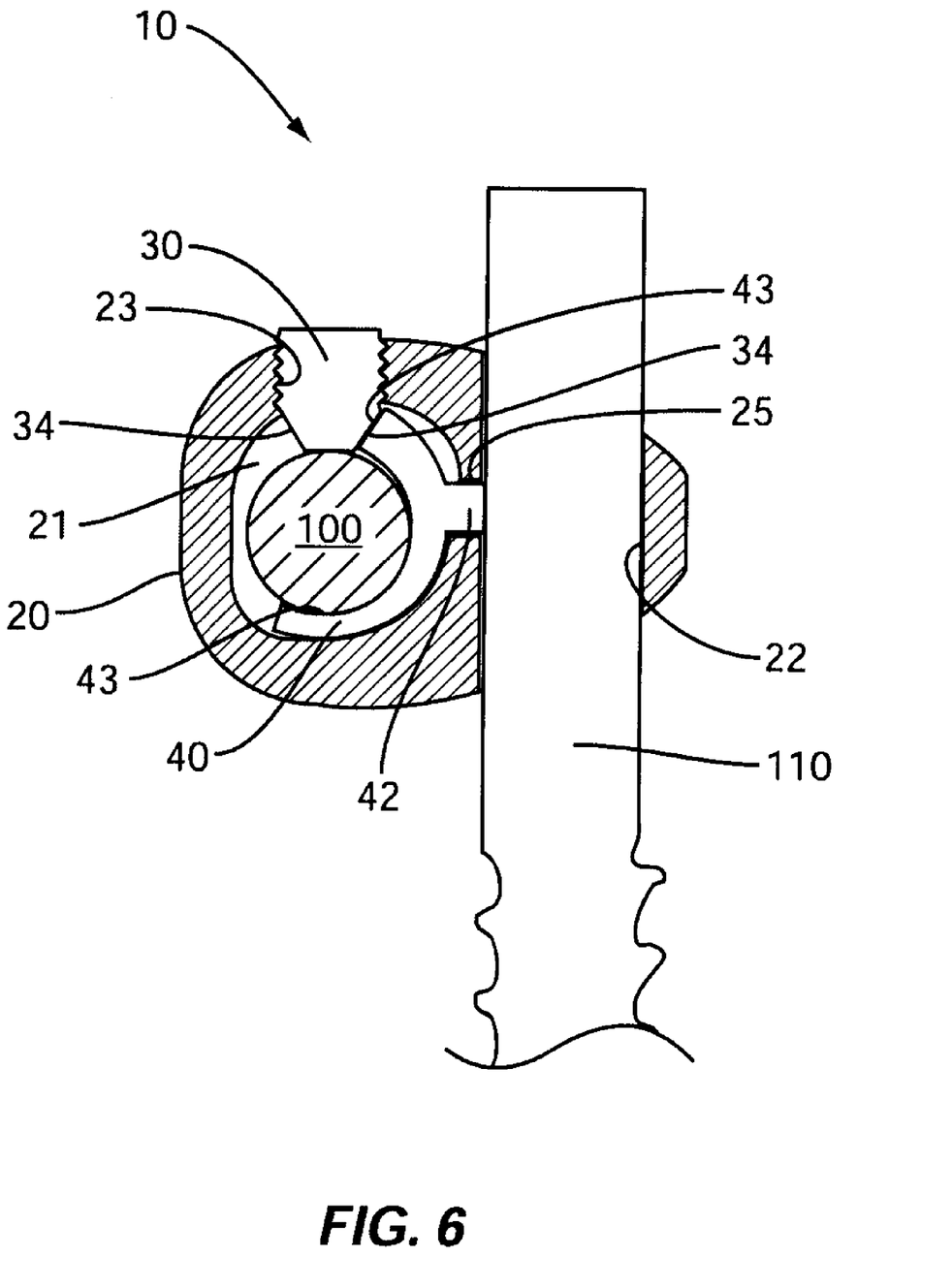
FIG. 6 is a sectional view of a connector that attaches a vertebral rod to an anchor according to one embodiment.

Cradle 40 may also include a post 42 that extends through an opening 24 in the body 20. The post 42 forms an axis to allow the cradle 40 to pivot to accommodate the vertebral rod 100 at various angular positions within the designated plane. The post 42 may attach to the body 20 at a point away from the anchor 110 as illustrated in FIGS. 4 and 5, or towards the anchor 110 as illustrated in FIG. 6. FIGS. 17 and 18 include the post 42 being formed by the entire end of the cradle 40.

The cradle 40 is positioned in the body 20 to allow the set screw 30 to extend into the first channel 21. The cradle 40 may be positioned in the body 20 to contact the set screw 30 as illustrated in FIG. 3, or may be positioned away from the set screw 30 as illustrated in FIG. 5.

In one embodiment, the cradle 40 is pivotal about an axis that extends through the post 42. The axis that extends through the post may be perpendicular to a centerline of the first channel 21. The cradle 40 may also be pivotal about an axis that does not extend through the post 42. In one embodiment, the second surface 44 contacts against the body such that the second surface 44 dictates the pivot axis. The second opening 24 in the body 20 that receives the post 42 may include a larger width to allow the cradle 40 to translate along the first channel 21.

The elements of the body 20, set screw 30, and cradle 40 may be used in various different combinations to create a variety of different connectors 10. The embodiment of FIGS. 3 and 18 include the cradle 40 encircling a majority of the vertebral rod 100. The first channel 21 that receives the vertebral rod 100 is in communication with the second channel 22 that receives the anchor 110. A section of the cradle 40 is positioned within space directly between the vertebral rod 100 and the anchor 110. The cradle 40 is further positioned to be contacted by the set screw 30.

The set screw 30 is threaded into the opening 23 in the body 20 with the contact sections 34 of the set screw 30 contacting both the cradle 40 and the vertebral rod 100. This contact applies a compressive force to secure the vertebral rod 100 against the cradle first surface 41. The contact also causes a section of the cradle 40 to be forced against the anchor 110 to secure the body 20 with the anchor 110. The cradle 40 is forced laterally against the anchor 110 partially because of the shaft 32 of the set screw 30 includes a conical section at the end that forms the contact surfaces 34 that contact against a corresponding angled surface 43 on the cradle 40. Further, the set screw 30 is positioned at an oblique angle relative to the anchor 110. The extent of offset between the vertebral rod 100 and the anchor 110 is reduced to a width of the cradle 40.

FIG. 4 illustrates an embodiment with the first channel 21 being separated from the second channel 22 by the body 20. A window 25 connects the opening 23 that receives the set screw 30 and the second channel 22 that receives the anchor 110. A piston 50 positioned within the window 25 includes a angled surface 51 that contacts the set screw 30 and a second surface 52 that contacts the anchor 110. The angled surface 51 faces away from the second channel 22, and the second surface 52 faces towards the second channel 22. The angled surface 51 may be positioned at an oblique angle with the centerline of the first opening 23. The first surface 51 may be positioned at an acute angle relative to the second surface 52. When the set screw 30 is tightened, a first section of contact surfaces 34 on the set screw 30 contact against the vertebral rod 100 and secures the vertebral rod 100 within the first channel 21. A second section of contact surfaces 34 is formed by a conical section with an angled contact surface 34 that contacts against the angled surface 51. This contact causes the piston 50 to translate into contact with the anchor 110 and secure the body 20. The second end 52 of the piston 50 may be positioned farther away from the first channel 21 after the translational movement than before.

Figure 8:
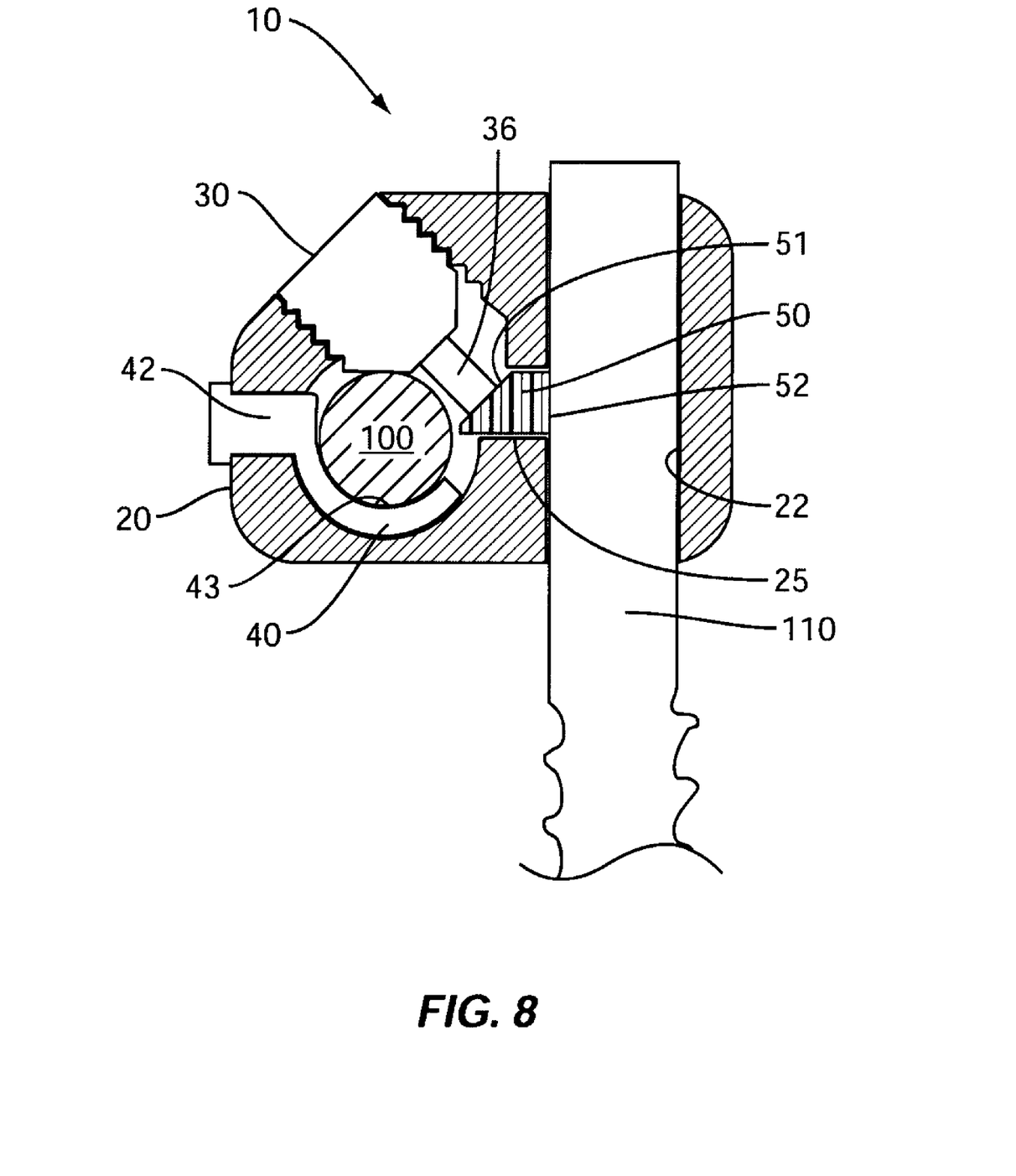
FIG. 8 is a sectional view of a connector that attaches a vertebral rod to an anchor according to one embodiment.

The piston 50 may be positioned within the body 20 in a variety of manners. In one embodiment, piston 50 is maintained by a snap fit mechanical stop. In another embodiment, the window 25 is sized to contain the piston 50 and prevent escape from the body 20 while still allowing for relative movement with the body 20. FIG. 8 includes a connector 36 that attaches the piston 50 to the set screw 30. The connector 36 positions the piston 50 accordingly as the set screw 30 moves within the body 20. The piston 50 may also be keyed with the body 20 to prevent twisting or rotation during translational movement. The piston 50 may include one or more tabs that extend outward and fit within corresponding slots in the body 20.

FIG. 5 includes an embodiment with the opening 23 in the body 20 angled to place the set screw 30 into both the first and second channels 21, 22. The first and second channels 21, 22 are in communication within the body 20. The opening 23 is positioned at an oblique angle relative to the second channel 22. During engagement, the set screw 30 contacts the vertebral rod 100 and secures the vertebral rod 100 to the body 20, and also contacts the anchor 110 and secures the body 20 to the anchor 110.

FIG. 6 includes an embodiment with a window 25 extending between the spaced-apart first and second channels 21, 22. The post 42 on the cradle 40 is positioned within the window 25. The cradle 40 further includes an angled edge 43 that is contacted by the angled contact surface 34 of the set screw 30. When the set screw 30 is engaged, the set screw 30 applies a force to secure the vertebral rod 100 to the body 20. The angled contact surface 34 of the set screw 30 also contacts the angled edge 43 causing the cradle 40 to translate towards the second channel 22 and apply a force on the anchor 110 and secure the body 20 to the anchor 110.

Figure 10:
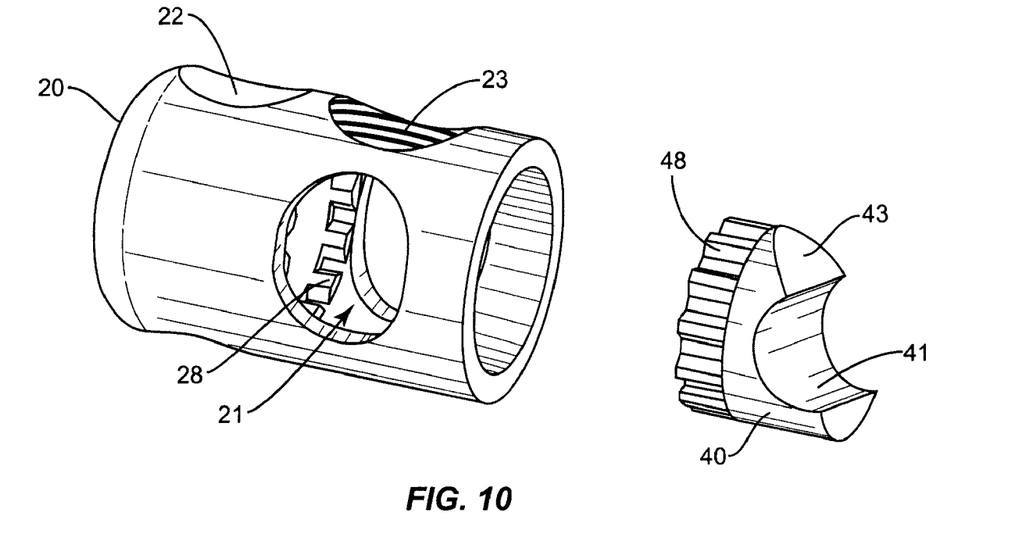
FIG. 10 is an exploded perspective view of a body and cradle according to one embodiment.
Figure 11:
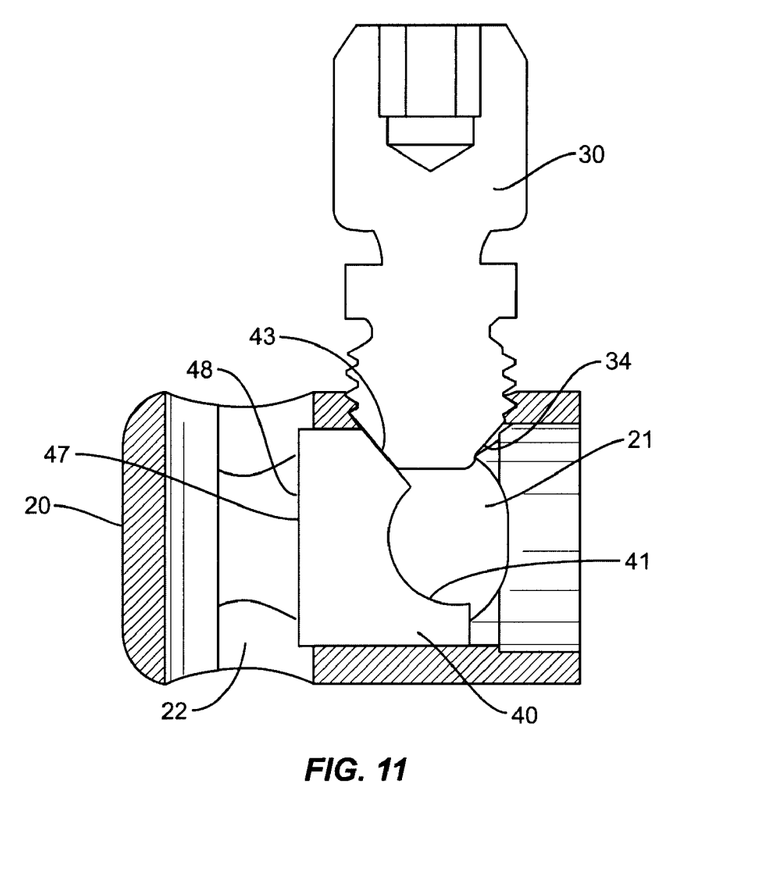
FIG. 11 is a sectional view of a body, cradle and set screw according to one embodiment.

The cradle 40 may also include teeth 48 that engage with corresponding teeth 28 in the body 20 as illustrated in FIGS. 10 and 11. The teeth 48 are positioned on an opposite lateral side of the cradle 40 from the first surface 41. Teeth 48 may extend around a limited section or the entire periphery of the cradle 40. Corresponding teeth 28 are positioned within an interior of the body 20 between the first and second channel 21, 22. Teeth 28 are shaped and size to engage with the teeth 48 when the cradle 40 translates within the body 20. Prior to engagement with the set screw 30, the angled surface 43 may be positioned at an oblique angle relative to a centerline of the first opening 23. As illustrated in FIG. 11, cradle 40 includes an angled surface 43 that is contacted by the set screw 30. This contact causes the cradle 40 to translate with the teeth 48 on the cradle 40 engaging with the teeth 28 on the body 20. The translation movement may be away from the first channel 21. This engagement maintains the angular position of the cradle 40 within the body 20. The cradle 40 also extends into the second channel 22 to engage the anchor 110. In one embodiment, the cradle 40 is positioned within an interior space within the body. One of both of the plurality of first and second teeth may be positioned perpendicularly to the second channel 22.

Figure 12:
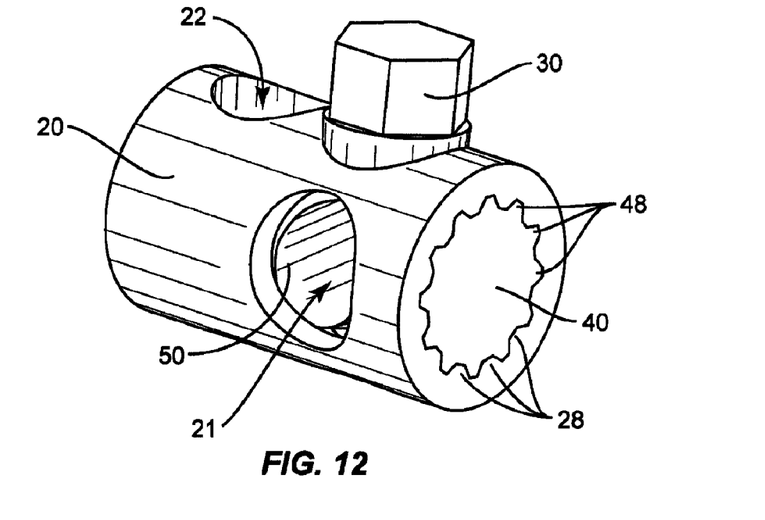
FIG. 12 is a perspective view of a body, cradle and set screw according to one embodiment.
Figure 13:
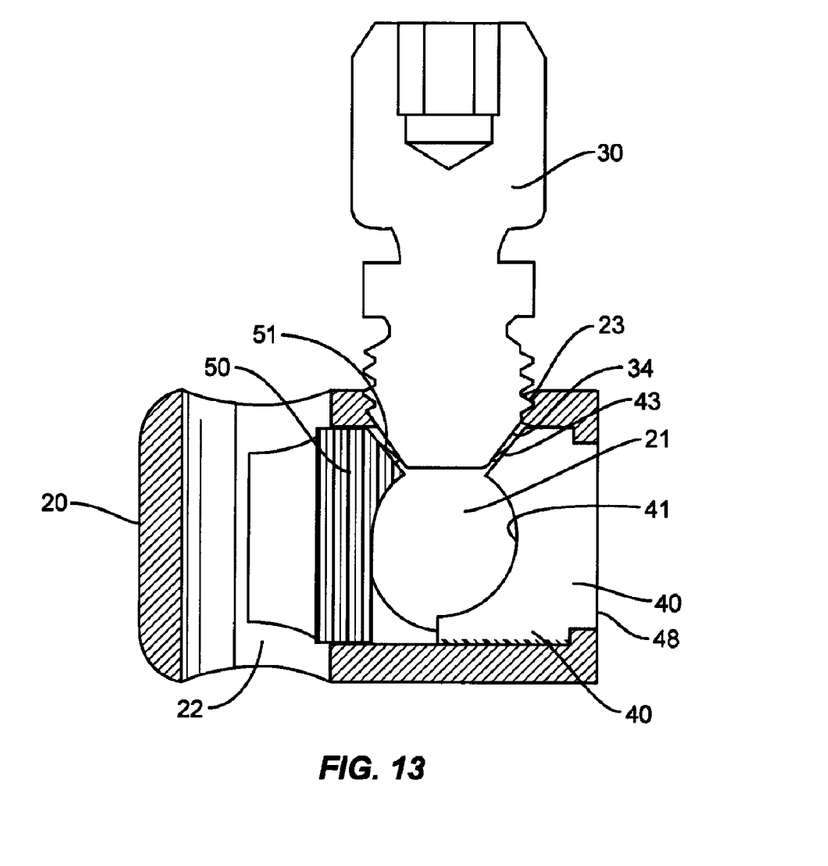
FIG. 13 is a section view of a body, cradle and set screw according to one embodiment.

FIGS. 12 and 13 include a similar embodiment with the cradle teeth 48 positioned away from and on an opposite side of the opening 23 from the second channel 22. A piston 50 is also positioned within the body 20 on an opposite side of the opening 23 from the cradle 40 and towards the second channel 22. In an initial position, the cradle 40 is positioned within an interior of the body 20 with the teeth 48 disengaged from the corresponding teeth 28. This position allows for the cradle 40 to rotate within the body 20 to accommodate the vertebral rod 100 at various angular positions. Once the angle is established, the set screw 30 is inserted into the opening 23 with the contact surface 34 contacting against the angled surface 43 of the cradle 40 and angled surface 51 of the piston 50. The contact with surface 43 causes the cradle 40 to translate in a first direction causing the cradle teeth 48 to engage with teeth 28 and lock the angular position of the cradle 40. Contact with surface 51 causes translation of the piston 50 in an opposite second direction to lock against the anchor 110. The piston 50 may be keyed into the body 20 to limit the contact to causing just translational movement. In one embodiment, the shape of the piston 50 allows for just translational movement.

Figure 14:
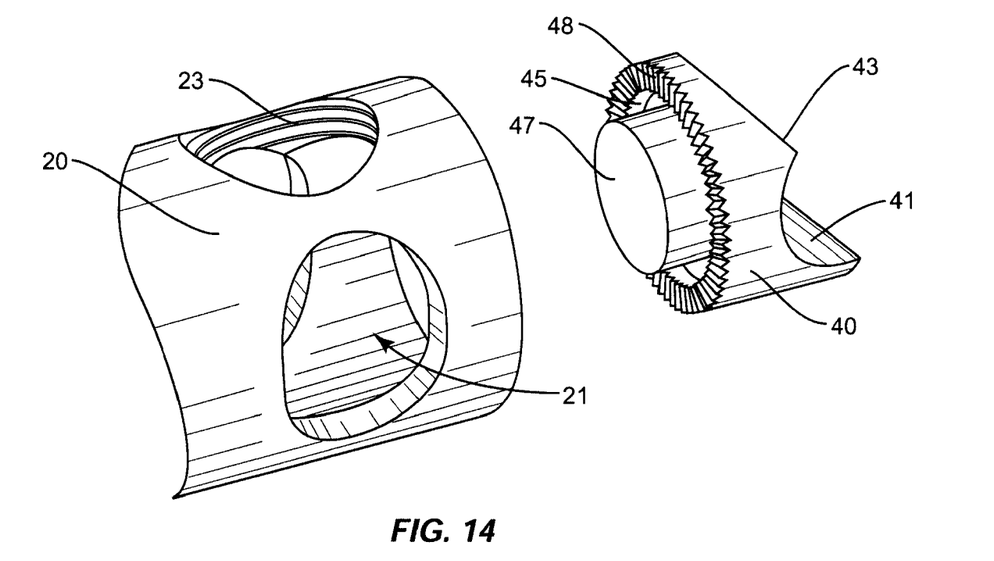
FIG. 14 is an exploded perspective view of a body and cradle according to one embodiment.
Figure 15:
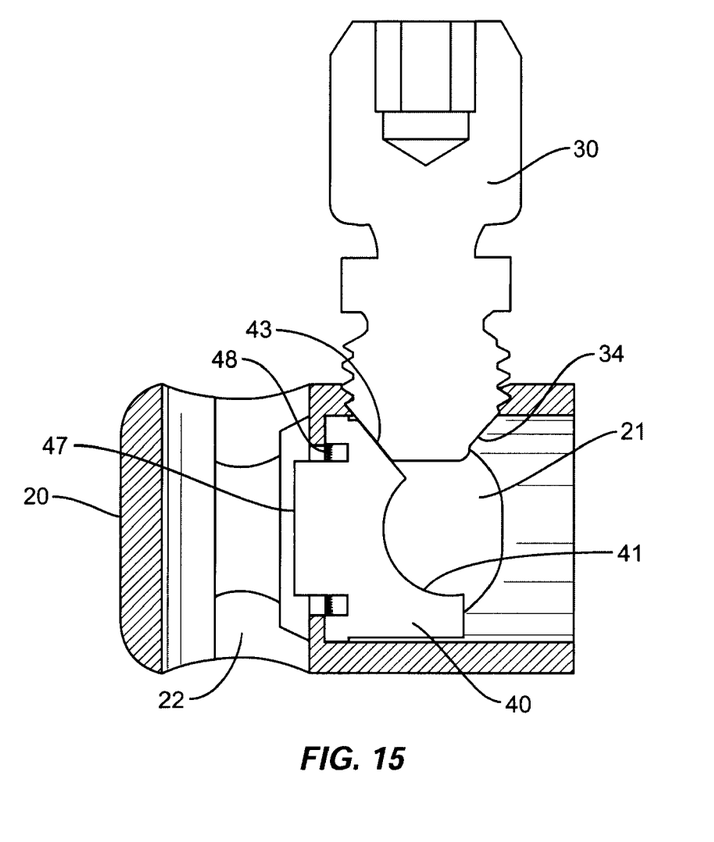
FIG. 15 is a sectional view of a body, cradle and set screw according to one embodiment.

FIGS. 14 and 15 include an embodiment with cradle teeth 48 along a first exterior face 45. A protrusion 47 extends outward beyond the first exterior face 45 and is sized to extend into the second channel 22 when the set screw 30 engages the angled surface 43 and the cradle 40 translates into engagement with the teeth 28 of the body 20.

FIG. 16 includes an embodiment with the first channel 21 in the body 20 including a ramped surface 26. The cradle 40 fits within the first channel 21 and includes a corresponding angled surface 46 that faces towards surface 26. The first and second channels 21, 22 are in communication and the cradle 40 is smaller than the space formed by the channels 21, 22 to allow the cradle 40 to move. During insertion of the set screw 30, the contact surface 34 contacts the vertebral rod 100 within the first surface 41. This contact causes the angled surface 46 to contact against surface 26. Continued insertion of the set screw 30 causes the cradle 40 to slide along the surface 26 and translate towards the second channel 22 and against the anchor 110.

The cradle 40 of FIG. 17 is positioned away form the channel 22. A piston 50 is positioned to be forced by the set screw 30 into the second channel 22 to lock the body 20 relative to the anchor 110. The cradle 40 further includes an end positioned away form the second channel 22 that is exposed through the end of the body 20.

FIG. 18 includes an embodiment with the cradle 40 extending around a majority of the vertebral rod 100. The cradle 40 includes an angled edge 43 that is contacted by the set screw 30. In one embodiment, the cradle 40 may deform and/or slide against the anchor 110 due to the contact with the set screw 30.

The anchor 110 includes a distal section that engages with the vertebral member 200. The distal section may include threads to thread into an opening formed in the vertebral member 200. The distal section may also include other attachment structures, including but not limited to hooks and clips. The proximal end extends upward beyond a surface of the vertebral member 200. The proximal end may include a smooth exterior surface or may be threaded.

The vertebral rod 100 may have a variety of lengths to extend along the spine and support one or more vertebral members 200. The vertebral rod 100 may include a variety of cross-sectional shapes, including circular as disclosed above. In one embodiment, the vertebral rod 100 is constructed from PEEK. The vertebral rod 100 may also be constructed of a variety of materials including metals, polymers, ceramics, and combinations thereof. Examples include but are not limited to titanium, stainless steel, cobalt chromium, silicone, silicone-polyurethane copolymer, and calcium phosphate.

One embodiment includes accessing the spine from an anterior approach to the spine. Other applications contemplate other approaches, including posterior, postero-lateral, antero-lateral and lateral approaches to the spine, and accessing other regions of the spine, including the cervical, thoracic, lumbar and/or sacral portions of the spine.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. In one embodiment, the cradle 40 is attached to the body 20 opposite from the set screw opening 23. The present embodiments are, therefore, to be considered in all respects as illustrative and not restrictive, and all changes coming within the meaning and equivalency range of the appended claims are intended to be embraced therein.

What is claimed is:

1. A connector to attach a vertebral rod to an anchor comprising:

a body including a first channel extending through opposing lateral sides to receive the vertebral rod and a second channel extending through opposing inferior and superior sides to receive the anchor, a centerline of the first channel being offset from a centerline of the second channel, the body further including a first opening positioned away from the opposing lateral sides and extending into the first channel;

a set screw with a head at a first end and a contact surface at a second end, the set screw configured to be positioned in an engaged orientation in the first opening with the contact surface in the first channel to contact the vertebral rod;

a cradle positioned in the body and including a curved first surface that faces towards the first channel and an opposite second surface that faces towards the second channel, the cradle including an angled end between the first and second surfaces that is positioned in proximity to the first opening; the cradle positioned in the body for the angled surface to be contacted by the contact surface when the set screw is in the engaged orientation to move the cradle relative to the body and position the second surface into the second channel; and a second opening in the body positioned away from the opposing lateral sides and extending into the first channel, the second opening being positioned on an opposite side of the first channel from the second channel, the second opening sized to receive a post on the second surface of the cradle.

2. The connector of claim 1, wherein the second surface includes an outwardly extending post that is positioned in the second channel when the set screw is in the engaged orientation.

3. The connector of claim 1, wherein the cradle is pivotal relative to the body about an axis that extends through the post with the axis being perpendicular to the centerline of the first channel.

4. The connector of claim 1, wherein the second opening includes a tapered shape with a width that decreases towards a bottom edge of the body.

5. The connector of claim 1, wherein a centerline of the first opening is parallel with the centerline of the second channel.

6. The connector of claim 1, wherein the second surface of the cradle and a surface of the first channel each include splines that extend perpendicularly with the centerline of the second channel.

7. The connector of claim 1, wherein the first surface of the cradle forms an arc greater than 180 degrees to extend around a majority of the vertebral rod.

8. The connector of claim 1, wherein a width of the second opening measured along the first channel is larger than a width of the post to allow the cradle to translate along the first channel.

* * * * *